United States Patent

An

[11] Patent Number: 5,852,300
[45] Date of Patent: Dec. 22, 1998

[54] DEVICE FOR SENSING A FLAT ZONE OF A WAFER FOR USE IN A WAFER PROBE TESTER

[75] Inventor: Sang-bae An, Kyonggi-do, Rep. of Korea

[73] Assignee: Samsung Electronics Co., Ltd., Suwon, Rep. of Korea

[21] Appl. No.: 825,222

[22] Filed: Mar. 19, 1997

[30] Foreign Application Priority Data

Oct. 8, 1996 [KR] Rep. of Korea ............ 96-44624

[51] Int. Cl.$^6$ .................................................. G01N 21/86
[52] U.S. Cl. ........................ 250/559.22; 250/208.2; 250/548; 356/150; 356/400
[58] Field of Search ..................... 250/559.22, 208.2, 250/548, 559.4; 356/150, 399–400

[56] References Cited

U.S. PATENT DOCUMENTS

| | | | |
|---|---|---|---|
| 4,559,452 | 12/1985 | Igaki et al. | 356/386 |
| 4,907,035 | 3/1990 | Galburt et al. | 356/150 |
| 5,159,202 | 10/1992 | Ametani | 356/400 |
| 5,452,078 | 9/1995 | Cheng | 250/548 |

FOREIGN PATENT DOCUMENTS

WO 95/00819  1/1995  WIPO .................... 356/150

Primary Examiner—Stephone B. Allen
Attorney, Agent, or Firm—Jones & Volentine, L.L.P.

[57] ABSTRACT

A sensing device, for installation in a wafer probe tester for sorting wafers according to the quality thereof, includes a main body for mounting on the wafer probe tester, an upper member and a lower member extending from the main body to define an open area therebetween for insertion of any one of different sized wafers, a plurality of light emitting devices spaced apart at fixed intervals and installed on the upper member, a plurality of light receiving devices spaced apart at respective locations opposed to the light emitting devices across the open area and installed on the lower member, and a control circuit, connected to the light emitting devices and the light receiving devices, for detecting a flat zone of any one of the different sized wafers inserted into the open area. The different sized wafers include 4 inch, 5 inch and 6 inch wafers.

14 Claims, 7 Drawing Sheets

Flat zone
sensing section

DEVICE FOR SENSING A FLAT ZONE OF A WAFER FOR USE IN A WAFER PROBE TESTER

BACKGROUND OF THE INVENTION

1. Field of the Invention

The present invention relates to a sensing device for sensing wafer flat zones of wafers which have been subjected to an etching process, a deposition process, an implantation process, and so on, and which have been loaded on a wafer probe tester to be sorted according to the quality thereof. More specifically, the invention relates to a device having sensors installed at each of equivalent locations of different sized wafers (e.g. 4, 5, 6 inch wafers) such that the sensors automatically and simply detect the flat zones of the various sized wafers. This results in an enhanced loading operation efficiency and, at the same time, a reduced wafer loading time.

2. Description of the Related Art

Generally, in the manufacturing of semiconductors, wafers which have first been subjected to an etching process, a deposition process, an implantation process, and so on, are then subjected to a quality sorting process (in other words, a wafer probe process) before being diced for fabrication into chips. The wafer probe process is performed by a wafer probe tester, equipped with an extremely delicate probe and coupled to a computer, for testing the electric characteristics of the chips. Then, chips which test poorly are given a black mark for easy discrimination. Since a wafer consists of several hundreds of chips having complex electric characteristics, the wafer probe test is accomplished in conjunction with a computer which allows for mass testing.

The wafer probe tester generally includes a conventional sensing device for sensing flat zones of the wafers to be tested for accurate alignment of the wafers on the tester. The conventional sensing device is shown in FIG. 1.

Figure 1:
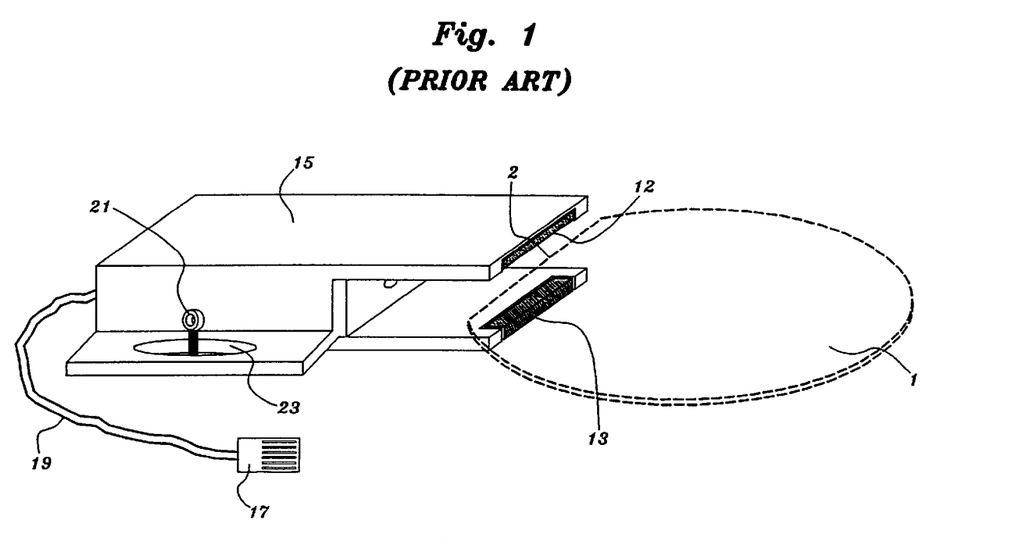
FIG. 1 is a schematic diagram of a conventional wafer flat zone sensing device.

Referring to FIG. 1, the conventional wafer flat zone sensing device of the wafer probe tester includes: a flat zone sensor formed by the combination of a light emitting diode (LED) 12 and a photo diode 13 (or a photo transistor); a body 15 for mounting of the LED 12 and the photo transistor 13 thereon, and fixed to a base frame (not shown) of the tester; an interface adapter 17 for interfacing with a controller by exchanging signals of the LED 12 and the photo transistor 13 via a cable 19; and a screw member 21 adapted for extension through a hole formed in the body 15, for fixing the body 15 at the base frame of the tester. The thus composed sensing device is configured to sense the so-called flat zone 2 of the wafer 1.

Figure 2:
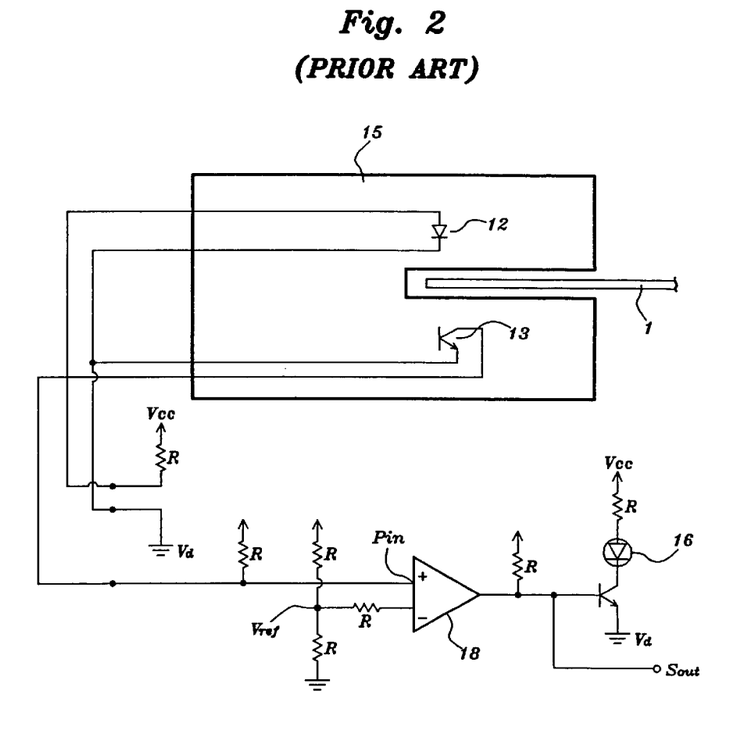
FIG. 2 is a circuit diagram of a conventional sensing circuit for the conventional sensing device.
Figure 3:
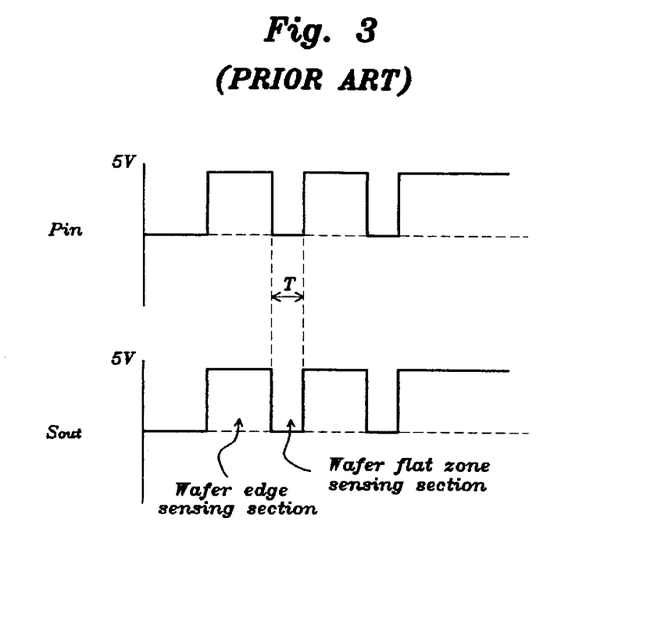
FIG. 3 is a timing chart for explaining the operation of the circuit of FIG. 2.

The circuit for driving the LED 12 and the photo transistor 13 of the flat zone sensor is illustrated in FIG. 2. When a wafer 1 is introduced into the angular c-shaped space between the LED 12 and the photo transistor 13 of the base 15, and is rotated by a device (not shown) of the tester, the on/off state of the photo transistor 13 is controlled according to the orientation of the wafer flat zone 2, and inputted into a comparator 18. When the remaining edge of the wafer 1 is located in the c-shaped space, the light from the LED 12 is intercepted by the wafer. On the other hand, when the flat zone 2 of the wafer 1 is located in the c-shaped space, the light from the LED 12 is directed onto the photo transistor 13. In this manner, when the light from the LED 12 is supplied to the photo transistor 13, a low level signal is inputted into an input terminal $P_{in}$ of the comparator 18 which is connected to the collector of the photo transistor 13. When the light from the LED 12 is intercepted by the wafer and not supplied to the photo transistor 13, a high level signal is inputted into the input terminal $P_{in}$ of the comparator 18. If the voltage of the high level signal inputted into the input terminal $P_{in}$ of the comparator 18 is set to be the same as or higher than the reference voltage inputted into the other input terminal of the comparator 18, the output of the comparator 18, that is, signal $S_{out}$ input into a microprocessor unit (MPU, not shown) of the tester, becomes a low level when the flat zone 2 of the wafer 1 is sensed and becomes a high level when the remaining edge of the wafer 1 sensed, as shown in FIG. 3. The flat zone is sensed during the low level interval T of the signal $S_{out}$ in FIG. 3. The interval T is approximately 250 ms in the EG2001X PROBE STATION.

Referring again to FIG. 2, an indicating lamp 16 is adapted to be on when the output of the comparator 18 is high, in other words, when the remaining edge of the wafer is sensed. Reversely, when the output of the comparator 18 is low, that is, when the flat zone is sensed, the indicating lamp 16 is off. Accordingly, by monitoring the indicating lamp 16 driven by the signal $S_{out}$ from the comparator 18, the wafer flat zone can be sensed. Also, in FIG. 2, the reference letter R represents bias resistances and resistances for adjusting current/voltage, each having a unique resistance value. The reference letters Vcc and Vd represent a power supply and ground, respectively.

The conventional sensing device as described above suffers a drawback in that the flat zone sensor formed by the LED 12 and the photo transistor 13 must be relocated and fixed for each of different sized wafers (e.g. 4, 5 and 6 inch wafers). For accurate setting of the sensor, the relocation must be accompanied by consecutive monitoring of the indicating lamp 16. In other words, to sense the various flat zones of the wafers and to probe the different sized wafers, the conventional flat zone sensor requires manual movement, fixation and adjustment operations. This results in the disadvantage of increased time consumption caused by the increased preparatory work time associated with each of the different sized wafers.

SUMMARY OF THE INVENTION

It is therefore an object of the present invention to provide a sensing device for automatically sensing flat zones of different sized wafers (i.e., 4, 5 and 6 inch wafers) without the need for extra manual work, by means of installing a plurality of flat zone sensors at each of respective equivalent locations of the different sized wafers. The wafer loading operation efficiency is thus enhanced, and at the same time, the preparatory work time associated with the use of different sized wafers is reduced.

To achieve the above and other objects of the invention, the sensing device of the invention, for installation in a wafer probe tester for sorting wafers according to the quality thereof, includes: a main body for mounting on the wafer probe tester; an upper member and a lower member extending from said main body to define an open area therebetween for insertion of any one of different sized wafers; a plurality of light emitting devices spaced apart at fixed intervals and installed on said upper member; a plurality of light receiving devices spaced apart at respective locations opposed to said light emitting devices across said open area and installed on said lower member; and a control circuit, connected to said light emitting devices and said light receiving devices, for detecting a flat zone of any one of the different sized wafers inserted into said open area.

Preferably, the device is configured to handle different sized wafers of 4 inches, 5 inches and 6 inches.

Preferably, the plurality of light emitting devices are light emitting diodes (LEDs) and the plurality of light receiving devices are photo transistors having on/off states dependent on the reception of the light from the light emitting diodes.

Preferably, the plurality of light emitting devices and the plurality of light receiving devices are arranged and installed for sensing 4, 5 and 6 inch wafers, and the interval between each adjacent pair of light emitting devices and between each adjacent pair of light receiving devices is one inch.

Preferably, the open area is an angular c-shaped area defined by the main body and the upper and lower members.

Preferably, the upper and the lower members are plates extending parallel to each other and spaced apart from each other by a predetermined distance, and also preferably, the light receiving devices are installed on the upper plate and the light emitting devices are installed on the lower plate.

DETAILED DESCRIPTION OF THE PREFERRED EMBODIMENTS

The wafer flat zone sensing device for a wafer probe tester, according to the present invention, as well as a preferred mode of use, will be hereinafter described in detail, referring to accompanying drawings. For description purposes, elements having basically the same function as previously described conventional elements are identified using common reference numbers throughout the drawings, and detailed descriptions thereof are omitted below.

The wafer flat zone sensing device of the invention automatically senses the flat zones of different sized wafers (e.g. 4, 5 and 6 inch wafers) without manual intervention, by the inclusion of a plurality of flat zone sensors at locations corresponding to the different sized wafers. Accordingly, the preparatory work time associated with the use of the different sized wafers is reduced.

Figure 4:
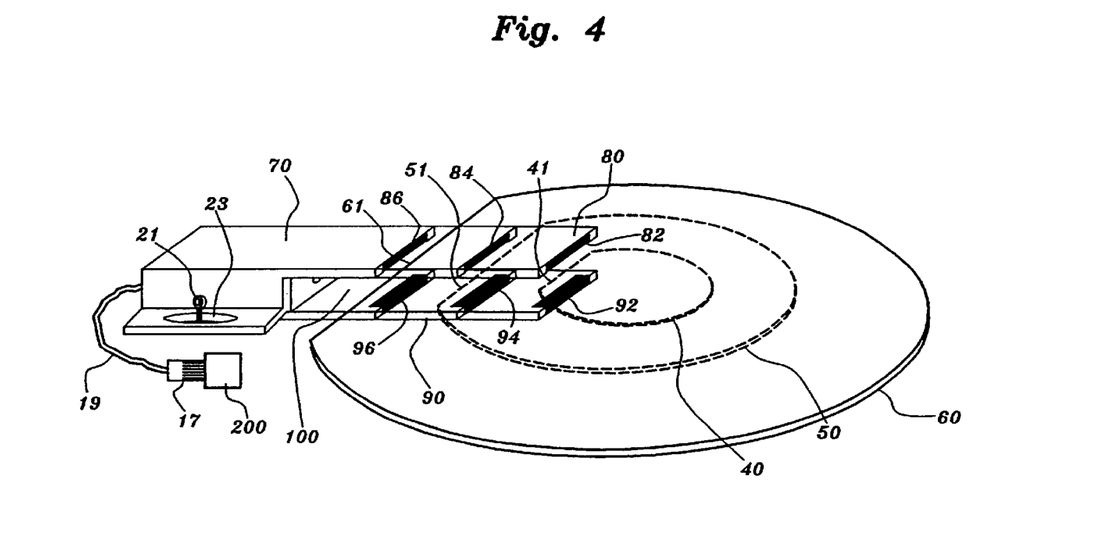
FIG. 4 is a schematic diagram of a wafer flat zone sensing device of the present invention.

Referring to FIG. 4, the device includes a body 70 mounted on a wafer probe tester (not shown) by screw member 21; an upper plate 80 and a lower plate 90 extending from the body 70 to define a space 100 for insertion of various sized wafers (e.g. 4 inch wafers 40, 5 inch wafers 50, and 6 inch wafers 60); a $1^{st}$ LED 82, a $2^{nd}$ LED 84 and a $3^{rd}$ LED 86 for emitting light and installed at fixed intervals on the upper plate 80; a $1^{st}$ photo transistor 92, a $2^{nd}$ photo transistor 94 and a $3^{rd}$ photo transistor 96 for receiving the light from the respective LEDs 82, 84 and 86, at positions on the lower plate which oppose the LEDs 82, 84 and 86 on the upper plate 80; and a control circuit 200 connected to the LEDs 82, 84 and 86 and the photo transistors 92, 94 and 96, for controlling the operation thereof and identifying the flat zones 41, 51 and 61 of the wafers 40, 50 and 60. The space 100 formed by the extended plates 80, 90 is preferably angular c-shaped as shown. The $1^{st}$ LED 82 and the $1^{st}$ photo transistor 92 are installed at the distal end of the upper plate 80 and the lower plate 90, respectively. The $2^{nd}$ LED 84 is installed on the inside of the upper plate 80, one inch away from the $1^{st}$ LED 82. The $2^{nd}$ photo transistor 94 is installed on the inside of the lower plate 90, one inch away from the $1^{st}$ photo transistor 92. The $3^{rd}$ LED 86 and the $_3$rd photo transistor 96 are installed on the inside of the upper plate 80 and the inside of the lower plate 90, one inch away from the $2^{nd}$ LED 84 and the $2^{nd}$ photo transistor 94, respectively.

Figure 5:
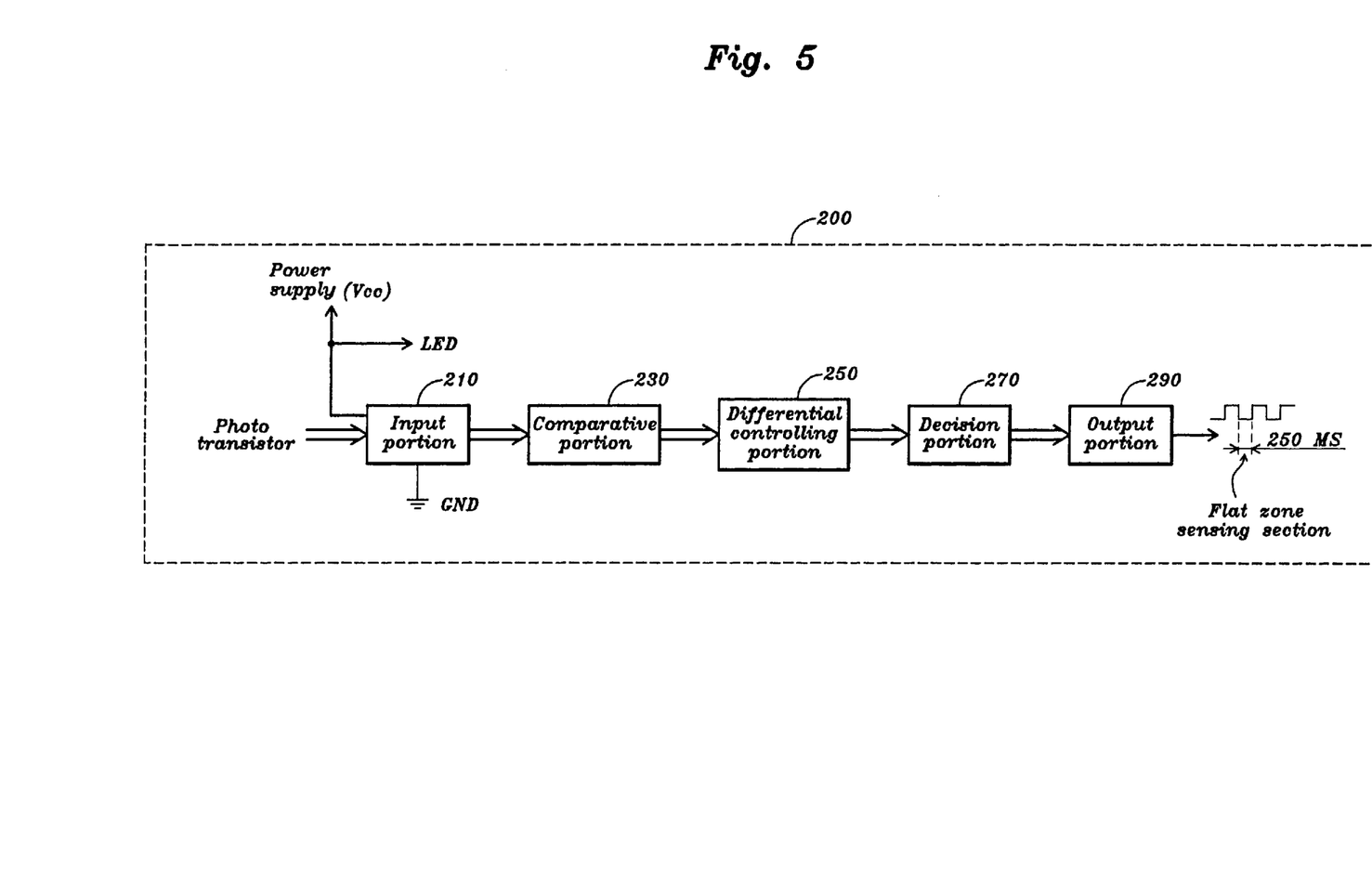
FIG. 5 is a block diagram of a controller for the sensing device of the present invention.

Referring now to FIG. 5, the control circuit 200 supplies the LEDs with power sufficient to cause the LEDs to emit, and includes an input portion 210 for receiving signals from the photo transistors 92, 94 and 96; a comparative portion 230 connected with the input portion 210, for comparing the signals from the photo transistors 92, 94 and 96 with reference signals and confirming the detection of the flat zones of the wafers 40, 50 and 60; a differential controlling portion 250 for differentiating signals from the comparative portion 230 and outputting preset control signals; a decision portion 270 for receiving signals from the differential controlling portion 250 and identifying the wafer flat zones; and an output portion 290 for outputting high/low signals in accordance with signals from the decision portion 270.

Figure 6:
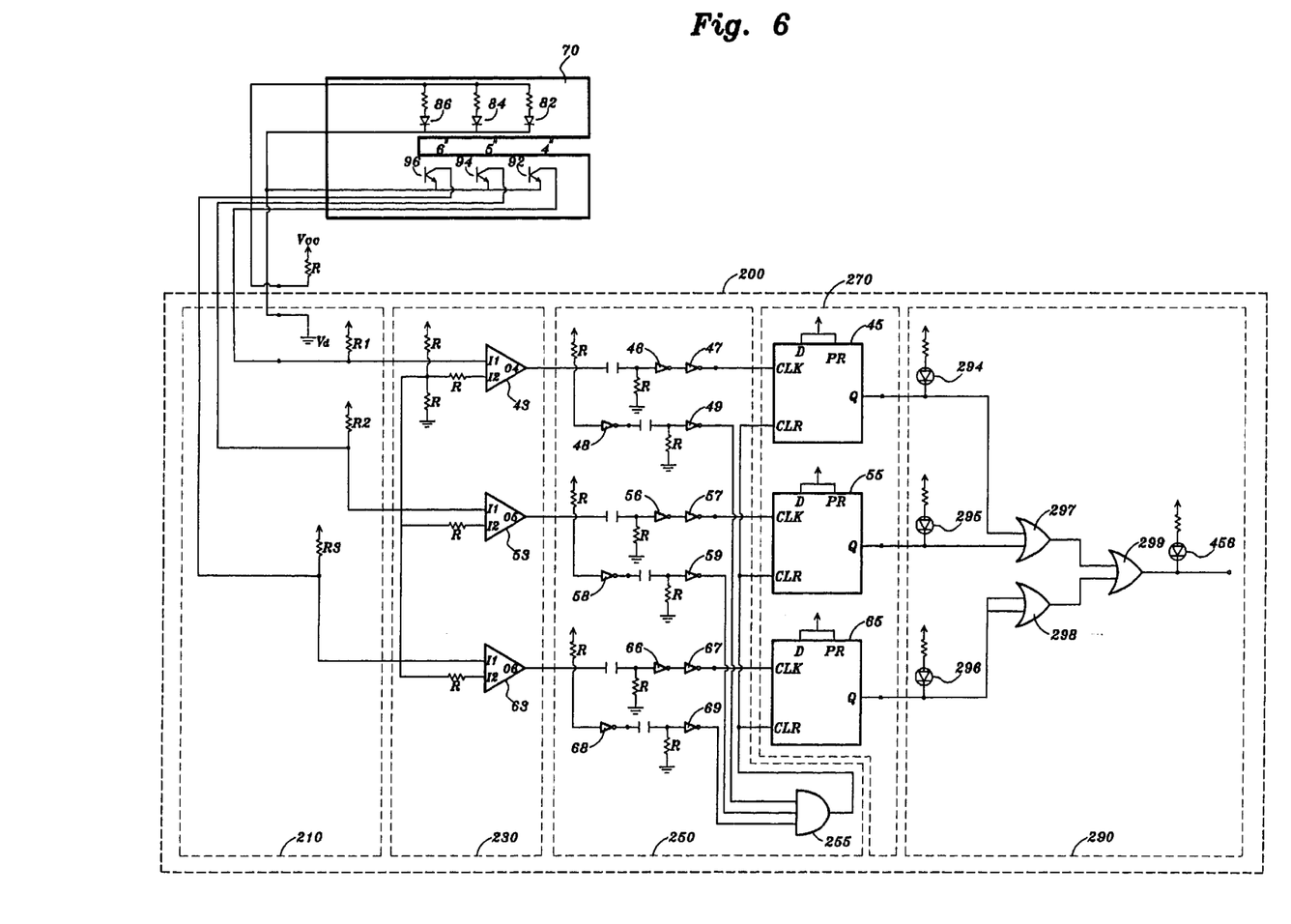
FIG. 6 is a detailed circuit diagram of the controller of FIG. 5.

Referring also to FIG. 6, the input portion 210 preferably includes three resistors RI, R2 and R3. The comparative portion 230 preferably includes three comparators 43, 53 and 63 and a plurality of resistors for providing reference voltages. The differential controlling portion 250 preferably includes a plurality of capacitors, resistors R, inverters 46–49, 56–59 and 66–69 and an AND gate 255. The decision portion 270 preferably includes three flip-flops 45, 55 and 65. The output portion 290 preferably includes a plurality of OR gates 297, 298, 299 and indicating lamps (i.e. indicating LEDs) 294, 295, 296 and 456. Reference numbers for the passive elements (i.e. resistors and capacitors) included in the control circuit 200 are omitted to simplify the description and drawings.

The operation of the sensing device composed as above will now be described.

As shown in FIG. 4, sensors of the $1^{st}$, $2^{nd}$ and $3^{rd}$ LEDs 82, 84 and 86 and the $1^{st}$, $2^{nd}$ and $3^{rd}$ photo transistors 92, 94 and 96, which together sense the flat zones of the various sized wafers (i.e., the 4 inch wafers 40, 5 inch wafers 50 and 6 inch wafers 60), are installed at locations corresponding to the different sized wafers on the plates 80 and 90 extending from the body 70. The control circuit 200 is installed as shown in FIG. 6, for governing the operation of and reading the outputs of the sensors, and identifying the flat zones. The 1st set of the $1^{st}$ LED 82 and the $1^{st}$ photo transistor 92 senses flat zones 41 of the 4 inch wafers 40. The $2^{nd}$ set of the $2^{nd}$ LED 84 and the $2^{nd}$ photo transistor 94 senses flat zones 51 of the 5 inch wafers 50. The $3^{rd}$ set of the $3^{rd}$ LED 86 and the $3^{rd}$ photo transistor 96 senses flat zones 61 of the 6 inch wafers 60.

The signals derived from the photo transistors 92, 94 and 96 are inputted into the differential controlling portion 250 via the resistors of the input portion 210 and the comparators 43, 53 and 63 of the comparative portion 230. The processed signals of the differential controlling portion 250 are then applied to the clock pin CLK of each flip-flop 45, 55 and 65 of the decision portion 270. The outputs from the flip-flops 45, 55 and 65 are outputted through the OR gates 297, 298 and 299 of the output portion 290. Therefore, by monitoring the output signals from the OR gate 299 of the output portion 290, the wafer flat zones can be easily identified. The signals from the flip-flops 45, 55, 65 are outputted at a same timing as that of the operation of the related sensors of the LEDs 82, 84 and 86 and the photo transistors 92, 94 and 96.

Figure 7:
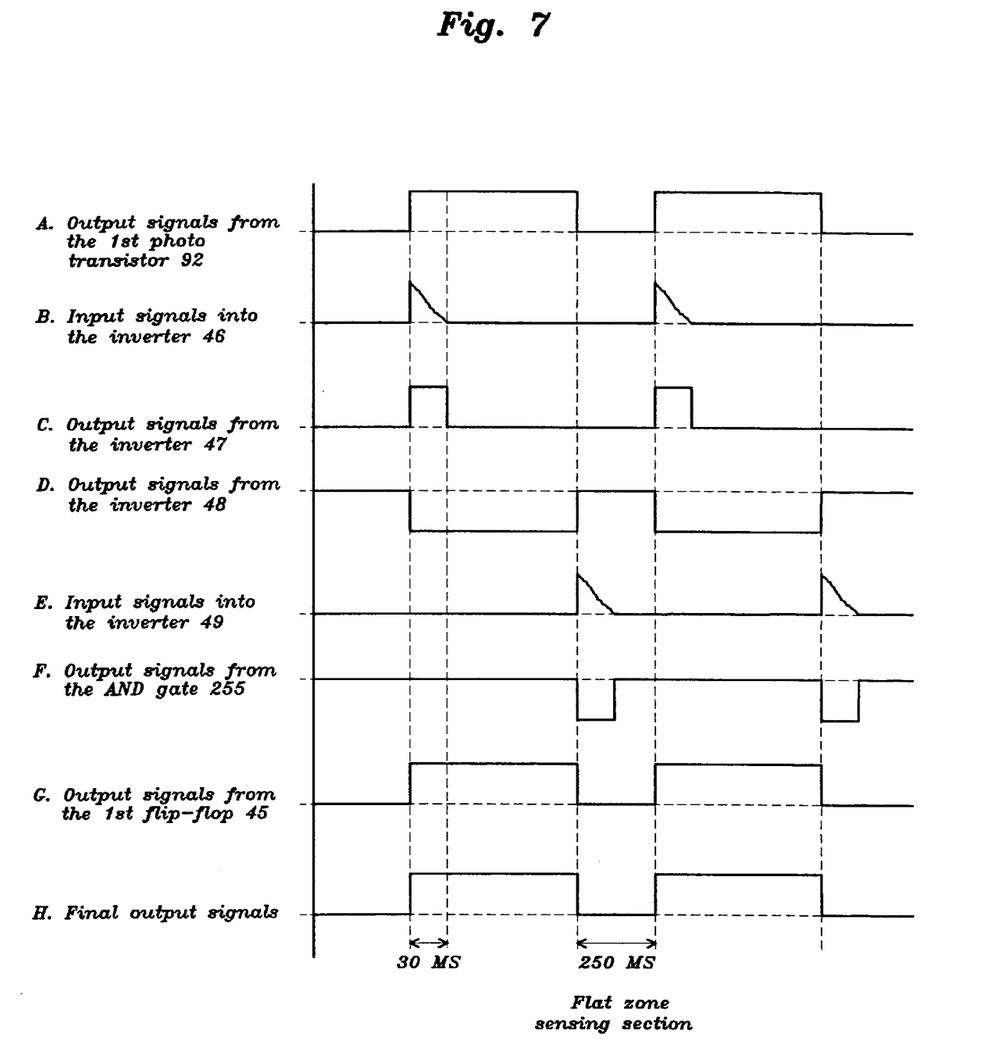
FIGS. 7,8 and 9 are timing charts for explaining the operation of the sensing device of the present invention with respect to the different sized wafers.

The operation of the sensing device for the flat zone 41 of the 4 inch wafers 40 is as follows. The 4 inch wafers 40 are sensed by the sensor of the $1^{st}$ LED 82 and the $1^{st}$ photo transistor 92. Then the $1^{st}$ photo transistor 92 generates a signal as shown in FIG. 7A. The signals are passed through the input portion 210 and inputted into an input terminal I1 of the $1^{st}$ comparator 43 in the comparative portion 230. This is followed by a signal comparison with the reference voltage inputted into the other input terminal I2 of the $1^{st}$ comparator 43. Then, a corresponding comparison signal is outputted through an output terminal O4 of the $1^{st}$ comparator 43. At this time, the compartor output signal is either high or low. A high signal means that the edge of the wafer 40 is sensed, while the low signal means that the flat zone 41 of the wafer 40 is sensed.

The output signal from the $1^{st}$ comparator 43 is inputted into the clock pin CLK of the 1st flip-flop 45 of the decision portion 270 through the differential controlling portion 250. The signal waveforms processed in the differential controlling portion 250 are shown in FIGS. 7B to 7F. FIG. 7B shows the signal waveform resulting when the signal from the 1st comparator 43 is differentiated by the capacitors and the resistors in the differential controlling portion 250, and inputted into the input terminal of the inverter 46. FIG. 7C shows the signal waveform resulting when the signal from the inverter 47 is inputted into the $1^{st}$ flip-flop 45 of the decision portion 270. FIG. 7D shows the signal waveform of the output from the inverter 48, i.e., the inverse of the signal output from the $1^{st}$ comparator 43. FIG. 7E shows the signal waveform resulting when the signal from the invertor 48 is differentiated by the capacitors and the resistors, and inputted into the invertor 49. FIG. 7F shows the signal waveform resulting when signals from AND gate 255 are inputted into the clear pin CLR of the 1st flip-flop 45.

When the edge of the 4 inch wafer is sensed, a high level signal is inputted into the clock pin CLK of the $1^{st}$ flip-flop 45 of the decision portion 270 as shown in FIG. 7C, while when the flat zone 41 of the 4 inch wafer is sensed, a low level signal is inputted into the clear pin CLR of the $1^{st}$ flip-flop 45 as shown in FIG. 7F. From the output terminal Q of the $1^{st}$ flip-flop 45, a signal waveform as shown in FIG. 7G is outputted. Signals outputted through the output terminal of the $1^{st}$ flip-flop 45 are finally outputted via the OR gates 297, 298 and 299 of the output portion 290 and inputted into a microprocessor unit (MPU, not shown) of the wafer probe tester. Thereby, the wafer flat zones are easily sensed. The $1^{st}$ indicating LED 294 of the output portion 290 is on when the edge of the 4 inch wafer is sensed, while it is off when the flat zone 41 of the 4 inch wafer 40 is sensed. Accordingly, the sensing state of the flat zone 41 can be recognized. Regardless of the different wafer sizes, the $4^{th}$ indicating LED 456 is on when the edge of the wafer is sensed and off when the flat zone of the wafer is sensed. In this manner, the sensing state of the flat zone of the wafers is visible by the $4^{th}$ indicating LED 456, regardless of the different wafer sizes.

Figure 8:
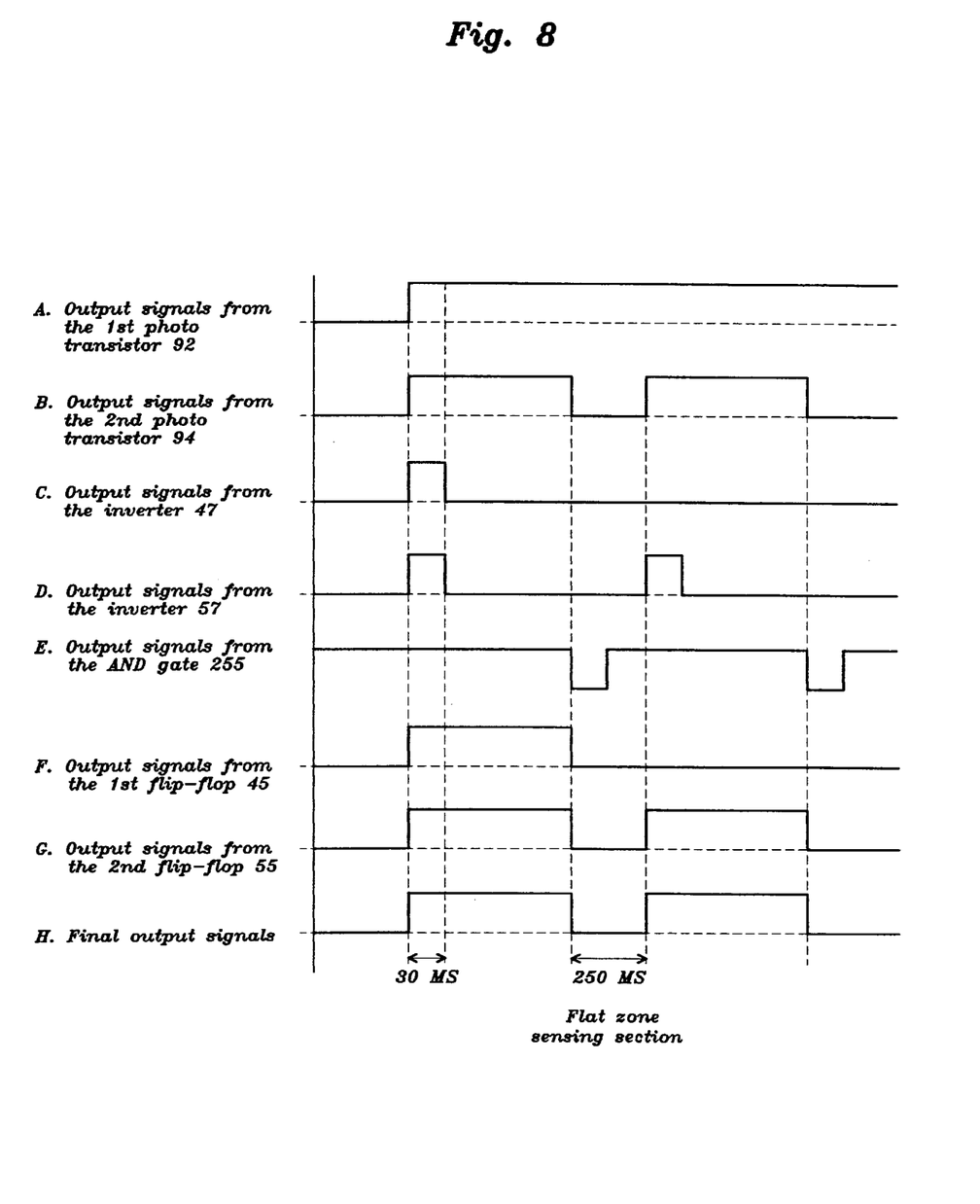

Now, the operation of the invention with regard to 5 inch wafers will be described with reference to FIGS. 6 and 8. In the case of 5 inch wafers, light from the $1^{st}$ LED 82 is intercepted by the 5 inch wafer itself and can not reach the $1^{st}$ photo transistor 92. Therefore, a high voltage (5V) is continuously supplied to the input terminal I1 of the $1^{st}$ comparator 43 and a high signal is continuously outputted from the output terminal O4 thereof. This is shown in FIG. 8A. Signals from the $1^{st}$ comparator 43 are inputted into the clock pin CLK of the $1^{st}$ flip-flop 45 of the decision portion 270 through the differential controlling portion 250, and then the output terminal Q becomes a high level.

Under this condition, the 5 inch wafers 50 are sensed by the sensor mechanism formed by the $2^{nd}$ LED 84 and the $2^{nd}$ photo transistor 94. The $2^{nd}$ photo transistor 94 generates signals as shown in FIG. 8B. The signals are passed through the input portion 210 and inputted into an input terminal I1 of the $2^{nd}$ comparator 53 in the comparative portion 230. This is followed by a signal comparison with the reference voltage inputted into the other input terminal I2 of the $2^{nd}$ comparator 53. Then, the corresponding comparison signal is outputted through an output terminal O5 of the $2^{nd}$ comparator 53. At this time, the output signals are either a high or a low level. A high level signal means that the edge of the wafer 50 is sensed, while a low level signal means that the flat zone 51 of the wafer 50 is sensed. The output signal as shown in FIG. 8B, from the $2^{nd}$ comparator 53, is inputted into the clock pin CLK of the $2^{nd}$ flip-flop 55 of the decision portion 270 through the differential controlling portion 250. The signal waveforms processed in the differential controlling portion 250 are shown in FIGS. 8C to 8F. FIG. 8C is the waveform signal resulting when signals from the inverter 47 are inputted into the $1^{st}$ flip-flop 45 of the decision portion 270, relative to the 4 inch wafer sensor formed by the $1^{st}$ LED and the $1^{st}$ photo transistor. FIG. 8D is the waveform signal resulting when the signal from the $2^{nd}$ invertor 57 is inputted into the $2^{nd}$ flip-flop 55 of the decision portion 270. FIG. 8E is the waveform signal resulting when the signal from AND gate 255 is inputted into the clear pin CLR of the $2^{nd}$ flip-flop 55. FIG. 8F is the signal waveform resulting when a signal is outputted from the $1^{st}$ flip-flop 45, relative to the 4 inch wafer sensor. Those skilled in this art should readily notice the similarity between the waveforms of FIGS. 7 and 8, the primary difference being the different starting points of the waveforms. When the edge of the 5 inch wafer 50 is sensed, a high level signal is inputted into the clock pin CLK of the $2^{nd}$ flip-flop 55 of the decision portion 270 as shown in FIG. 8D, while when the flat zone 51 of the 5 inch wafer 50 is sensed, a low level signal is inputted into the clear pin CLR of the $2^{nd}$ flip-flop 55 as shown in FIG. 8E. From the output terminal Q of the $2^{nd}$ flip-flop 55, a waveform as shown in FIG. 8G is outputted. Signals outputted through output terminal Q of the $2^{nd}$ flip-flop 55 are finally outputted via the OR gates 297, 298 and 299 of the output portion 290 as shown in FIG. 8H, and inputted into a microprocessor unit (MPU, not shown) of the wafer probe tester. Accordlingly, the wafer flat zones 51 are easily sensed. The $2^{nd}$ indicating LED 295 of the output portion 290 is on when the edge of the 5 inch wafer 50 is sensed, and it is off when the flat zone 51 of the 5 inch wafer 50 is sensed. Accordingly, the sensing state of the flat zone 51 can be seen. Regardless of the different wafer sizes, the $4^{th}$ indicating LED 456 is on when the edge of a wafer is sensed and off when the flat zone of a wafer is sensed. In this manner, the sensed state of the flat zone of the wafers is made visible by the $4^{th}$ indicating LED 456, regardless of the different wafer sizes.

Finally, the operation of the sensing device of the invention with regard to 6 inch wafers will be described with reference to FIGS. 6 and 9. In the case of 6 inch wafers, light from the $1^{st}$ and the $2^{nd}$ LEDs 82 and 84 is intercepted by the 6 inch wafer 60 itself and can not reach the $1^{st}$ and the $2^{nd}$ photo transistors 92 and 94. Therefore, a high voltage (5V) is continuously supplied to the input terminals I1 of the $1^{st}$ and the $2^{nd}$ comparators 43 and 53 and a high signal is continuously outputted from the output terminals O4 and O5 thereof. This is shown in FIGS. 9A and 9B. Signals from the $1^{st}$ and the $2^{nd}$ comparators 43 and 53 are inputted into the clock pins CLK of the $1^{st}$ and $2^{nd}$ flip flops 45 and 55 of the decision portion 270 through the differential controlling portion 250, and then the output terminals Q assume a high state.

Under this condition, the 6 inch wafers 60 are sensed by the sensor formed by the $3^{rd}$ LED 86 and the $3^{rd}$ photo transistor 96. The $3^{rd}$ photo transistor 96 generates signals as shown in FIG. 9C. The signals are passed through the input portion 210 and inputted into an input terminal I1 of the $3^{rd}$ comparator 63 in the comparative portion 230. This is followed by a signal comparison with the reference voltage inputted into the other input terminal I2 of the $3^{rd}$ comparator 63. Then, the signal is outputted through an output terminal O6 of the $3^{rd}$ comparator 63. At this time, the output signals are either high or low level. A high level signal means that the edge of the wafer 60 is sensed, while a low level signal means that the flat zone 61 of the wafer 60 is sensed. The output signal as shown in FIG. 9C, from the $3^{rd}$ comparator 63, is inputted into the clock pin CLK of the $3^{rd}$ flip-flop 65 of the decision portion 270 through the differential controlling portion 250. The signal waveforms processed in the differential controlling portion 250 are shown in FIGS. 9D to 9H. FIGS. 9D and 9E show the signal waveforms resulting when signals from the inverters 47 and 57 are inputted into the $1^{st}$ and the $2^{nd}$ flip flops 45 and 55 of the decision portion 270, relative to the 4 inch and the 5 inch wafer sensors of the $1^{st}$ and the $2^{nd}$ LEDs and the $1^{st}$ and the $2^{nd}$ photo transistors. FIG. 9F shows the signal waveform resulting when the signal from the $3^{rd}$ invertor 67 is inputted into the $3^{rd}$ flip-flop 65 of the decision portion 270. FIG. 9G shows the signal waveform resulting when the signal from AND gate 255 is inputted into the clear pin CLR of the $3^{rd}$ flip-flop 65. FIGS. 9H and 9I show the signal waveforms resulting when signals are outputted from the $1^{st}$ and the $2^{nd}$ flip-flops 45 and 55, relative to the 4 inch and 5 inch wafer sensors. Those skilled in this art should readily notice the similarity between the waveforms FIGS. 7, 8 and 9, the primary difference residing in the different starting points of the waveforms.

Figure 9:
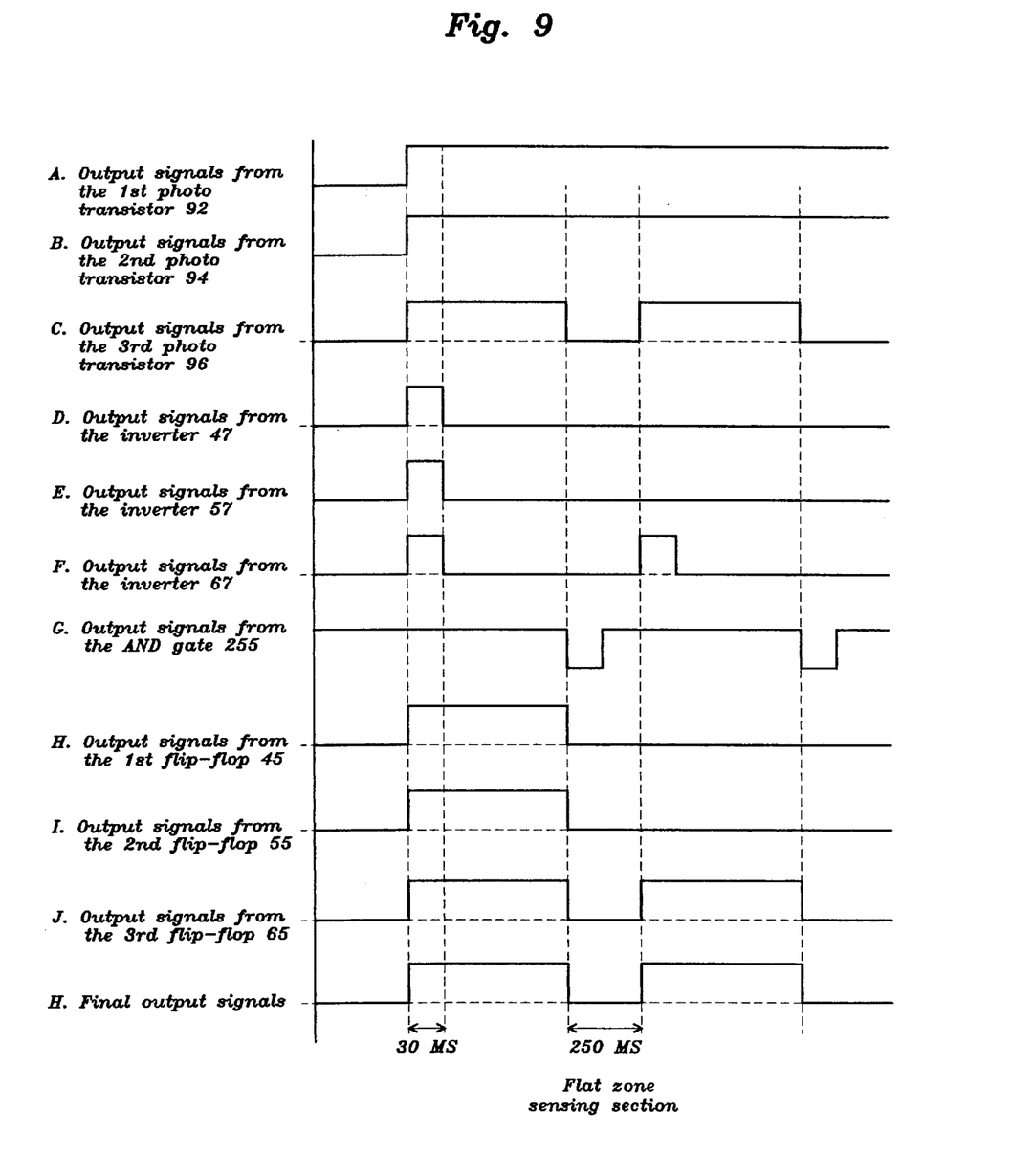

When the edge of the 6 inch wafer 60 is sensed, a high level signal is inputted into the clock pin CLK of the $3^{rd}$ flip-flop 65 of the decision portion 270 as shown in FIG. 9F, while when the flat zone 61 of the 6 inch wafer 60 is sensed, a low level signal is inputted into the clear pin CLR of the $3^{rd}$ flip-flop 65 as shown in FIG. 9G. From the output terminal Q of the $3^{rd}$ flip-flop 65, a waveform as shown in FIG. 9I is outputted. Signals outputted through output terminal Q of the $3^{rd}$ flip-flop 65 are finally outputted via the OR gates 297, 298 and 299 of the output portion 290 as shown in FIG. 9K, and inputted into the microprocessor unit (MPU, not shown) of the wafer probe tester. Accordingly, the wafer flat zones 61 of the 6 inch wafers 60 are easily sensed. The $3^{rd}$ indicating LED 296 of the output portion 290 is on when the edge of the 6 inch wafer 60 is sensed, and it is off when the flat zone 61 of the 6 inch wafer 60 is sensed. Accordingly, the sensing state of the flat zone 61 can be seen. Regardless of the different wafer sizes, the $4^{th}$ indicating LED 456 is on when the edge of any wafer is sensed and off when the flat zone of any wafer is sensed. In this manner, the sensed state of the flat zone of the wafers is visible by the $4^{th}$ indicating LED 456, regardless of the different wafer sizes.

The flip-flops 45, 55 and 65 of the decision portion 270 operate in such a manner that when the edges of related wafers are sensed, a high level signal is inputted into each related clock pin CLK thereof, while when the flat zones of the wafers are sensed, a low level signal is inputted into each related clear pin CLR thereof. The output terminals Qs of the $1^{st}$, the $2^{nd}$ and the $3^{rd}$ flip-flops 45, 55 and 65 generate a high or low signal in such a manner that when a high signal is inputted into the each related clock pin CLK, the output terminals Q output a high level signal, while when a high level signal is inputted into the each related clear pin CLR, the output terminals Q output a low level signal. Each output signal from the flip-flops 45, 55 and 65 is finally outputted through the OR gates 297, 298 and 299 of the output portion 290. When the output signal is a low the flat zone of the related wafer is sensed. The differential circuits formed of resistors and capacitors in the differential controlling portion 250 preferably output signals having approximately a 30 ms cycle.

In the invention, preferably the $1^{st}$, $2^{nd}$ and $3^{rd}$ comparators 43, 53 and 63 may be ordinary IC LM339s, the inverters 46–49, 56–59 and 66–69 may be ordinary IC 74HC05s, the $1^{st}$, $2^{nd}$ and $3^{rd}$ flip-flops 45, 55 and 65 may be ordinary IC 74LS74s, the AND gate 255 may be an ordinary IC 74HCII, the OR gates 297, 298 and 299 may be ordinary IC 74LS32s, and the resistors and the capacitors may be ordinary commercially available components.

As described above, the wafer flat zone sensing device of the wafer probe tester according to the invention has the advantageous effect of enhancing a loading operation efficiency and, at the same time, reducing wafer loading time, by the provision of sensors installed at each of equivalent locations of the different sized wafers (e.g., 4, 5 and 6 inch wafers) which enable the sensors to automatically and simply sense the flat zones of the various sized wafers.

What I claim is:

1. A sensing device for use in discriminating wafers said device comprising:

a main body;

an upper member and a lower member extending from said main body and spaced apart to define an open area sized to receive any one of different sized wafers inserted between said members;

a plurality of light emitting devices spaced apart from one another in a direction of insertion of the wafers and disposed on one of said upper and lower members;

a plurality of light receiving devices spaced apart from one another in said direction of insertion and disposed on the other of said upper and lower members at respective locations opposed to said light emitting devices, respectively, said light receiving devices each being operative to generate a signal indicative of whether the light receiving device is receiving light emitted from the light emitting devices disposed across therefrom; and a control circuit connected to said light receiving devices, said control circuit including comparing means for comparing signals generated from each of said light receiving devices with a reference signal, respectively, and for outputting comparison signals representative of the comparisons, differential controlling means for receiving the comparison signals produced by said comparing means, for differentiating the comparison signals, and for outputting control signals representative of the differentiating of the comparison signals, and decision means for receiving the control signals from said differential control means and, based on the control signals, for outputting signals indicative of a location where a flat zone of a wafer, inserted into said area between said upper and lower members, lies with respect to said light receiving devices in said direction of insertion of the wafers.

2. The sensing device of claim 1, wherein said light receiving devices are spaced sufficiently and said control circuit is configured to differentiate between 4 inch, 5 inch, and 6 inch wafers.

3. The sensing device of claim 1, wherein said plurality of light emitting devices are light emitting diodes.

4. The sensing device of claim 1, wherein said plurality of light receiving devices are photo transistors having on/off states dependent on the reception of light from said light emitting diodes.

5. The sensing device of claim 1, wherein said light emitting devices are spaced from each other by intervals of one inch in said direction of insertion of the wafer, said light receiving devices are spaced from each other by intervals of one inch in said direction of insertion, and said control signals are preset to yield indications of whether a 4, 5 or 6 inch wafer is inserted between said members.

6. The sensing devices of claim 2, wherein said light emitting devices are spaced from each other by intervals of one inch in said direction of insertion of the wafer, said light receiving devices are spaced from each other by intervals of one inch in said direction of insertion, and said control signals are preset to yield indications of whethere a 4, 5 or 6 inch wafer is inserted between said members.

7. The sensing device of claim 1, wherein said open area is an angular c-shaped area defined by said main body and said upper and lower members.

8. The sensing device of claim 1, wherein said upper and lower members are respective plates extending parallel to each other and spaced apart from each other by a predetermined distance.

9. The sensing device of claim 8, wherein said light receiving devices are disposed on said upper plate and said light emitting devices are disposed on said lower plate.

10. The sensing device of claim 1, wherein said control circuit further includes an output portion having a plurality of indicating devices operatively connected to said decision means so as to receive the signals generated thereby and based on the received signals indicate a sensed location of the flat zone of a wafer inserted between said members, and a common indicating device operatively connected to said decision means so as to receive any signal generated thereby and based on the received signal indicate a sensing of any flat zone of a wafer regardless of the size of the wafer.

11. The sensing device of claim 1, wherein said decision means outputs a low level signal as an indicator of a flat zone of a wafer lying at a location to one side of a respective said light receiving device with respect to said direction of insertion such that the respective light receiving device receives light from the light emitting device disposed across said open area therefrom, and a high level signal as an indicator of a peripheral edge portion of a wafer intercepting light emitted from a respective said light receiving device disposed across said open area therefrom.

12. A sensing device for use in sorting wafers, said device comprising:

a main body;

an upper member and a lower member extending from said main body and spaced apart to define an open area sized to receive any one of different sized wafers inserted between said members;

a plurality of light emitting devices spaced apart from one another in a direction of insertion of the wafers and disposed on one of said upper and lower members;

a plurality of light receiving devices spaced apart from one another in said direction of insertion and disposed on the other of said upper and lower members at respective locations opposed to said light emitting devices, respectively, said light receiving devices each being operative to generate a signal indicative of whether the light receiving device is receiving light emitted from the light emitting device disposed across therefrom; and a control circuit connected to said light receiving devices, said control circuit including a comparative portion comprising a plurality of comparators connected to said light receiving devices, respectively, and a plurality of resistors connected to said comparators and providing reference voltage such that each of said comparators compares the signal generated by a respective one of said light receiving devices with a reference voltage, a differential controlling portion comprising first signal inverters connected to said comparators, respectively second signal inverters, resistors connected to said second signal inverters, and an AND gate to which the second signal inverters are each connected, a decision portion comprising a plurality of flip-flops each having a CLK pin, a CLR pin, and an output terminal, the first signal inverters of said differential controlling portion being connected to the CLK pins of said flip-flops respectively, and the AND gate of said differential controlling portion being connected to the CLR pin of each of said flip-flops, and an output portion connected to the output terminals of the flip-flops of said decision portion, said output portion including a display where information from said decision portion is indicated.

13. The sensing device of claim 12, wherein said display comprises a plurality of light emitting diodes connected to the output terminals of said flip-flops, respectively.

14. The sensing device of claim 13, wherein said output portion also includes a plurality of OR gates connected to the output terminals of said flip-flops in series with said light emitting diodes, and a common light emitting diode connected to output terminals of said OR gates, the OR gates being configured to cause said common light emitting diode to emit light whenever any one of the other light emitting diodes is emitting light.

* * * * *